US012569604B2

(12) United States Patent
Millan-Galante

(10) Patent No.: US 12,569,604 B2
(45) Date of Patent: Mar. 10, 2026

(54) METHOD AND DEVICES FOR DETERMINING A TIME POINT FOR MEASURING PRESSURE MEASUREMENTS

(71) Applicant: Fresenius Medical Care Deutschland GmbH, Bad Homburg (DE)

(72) Inventor: Maria Millan-Galante, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 749 days.

(21) Appl. No.: 17/793,799

(22) PCT Filed: Jan. 27, 2021

(86) PCT No.: PCT/EP2021/051845
§ 371 (c)(1),
(2) Date: Jul. 19, 2022

(87) PCT Pub. No.: WO2021/151932
PCT Pub. Date: Aug. 5, 2021

(65) Prior Publication Data
US 2023/0057779 A1 Feb. 23, 2023

(30) Foreign Application Priority Data
Jan. 31, 2020 (DE) ..................... 10 2020 102 471.1

(51) Int. Cl.
*A61M 1/34* (2006.01)
*A61M 1/16* (2006.01)
*A61M 1/36* (2006.01)

(52) U.S. Cl.
CPC .......... *A61M 1/341* (2014.02); *A61M 1/1605* (2014.02); *A61M 1/342* (2013.01);
(Continued)

(58) Field of Classification Search
CPC .... A61M 1/341; A61M 1/1605; A61M 1/342; A61M 1/3609; A61M 2205/18;
(Continued)

(56) References Cited

U.S. PATENT DOCUMENTS 4,718,891 A 1/1988 Lipps
6,602,424 B1 8/2003 Kramer et al.
(Continued)

FOREIGN PATENT DOCUMENTS

DE 19823811 11/1999
EP 2377563 5/2012
(Continued)

OTHER PUBLICATIONS

Dialysis Procedures in Clinics and Practices: Technology and Clinic, Horl et al. (eds.), 2004, 40-44, 362-367, 28 pages (with English translation).
(Continued)

*Primary Examiner* — Leslie R Deak
(74) *Attorney, Agent, or Firm* — Fish & Richardson P.C.

(57) ABSTRACT

The present disclosure relates to a method for determining or recommending a time point for measuring a patient's pressure readings during a blood treatment session. The method encompasses monitoring the ultrafiltration rate with which the patient's blood is treated, a relative blood volume, and/or a sodium concentration or a change in any of these, for the existence of, or meeting any pre-determined criterion for the ultrafiltration, the relative blood volume, and/or the sodium concentration, or the change thereto. Furthermore, the method encompasses transmitting a signal to a blood pressure measuring device when the pre-determined criterion for the ultrafiltration rate, the relative blood volume, and/or the sodium concentration or the change thereto is met.

24 Claims, 5 Drawing Sheets

(52) U.S. Cl.
CPC ....... *A61M 1/3609* (2014.02); *A61M 2205/18*
(2013.01); *A61M 2205/3317* (2013.01); *A61M*
*2205/3331* (2013.01); *A61M 2230/207*
(2013.01); *A61M 2230/30* (2013.01)

(58) Field of Classification Search
CPC .. A61M 2205/3317; A61M 2205/3331; A61M
2230/207; A61M 2230/30
See application file for complete search history.

(56) References Cited

U.S. PATENT DOCUMENTS

| | | |
|---|---|---|
| 2004/0057037 A1 | 3/2004 | Ohishi et al. |
| 2012/0138533 A1 | 6/2012 | Curtis et al. |

FOREIGN PATENT DOCUMENTS

| | | |
|---|---|---|
| JP | H11-317 | 1/1999 |
| JP | 2000-000300 A | 1/2000 |
| JP | 2004-097781 A | 4/2004 |

OTHER PUBLICATIONS

International Search Report in International Appln. No. PCT/EP2021/
051845, mailed May 7, 2021, 20 pages (with English translation).

METHOD AND DEVICES FOR DETERMINING A TIME POINT FOR MEASURING PRESSURE MEASUREMENTS

CROSS-REFERENCE TO RELATED APPLICATIONS

The present application is the national stage entry of International Patent Application No. PCT/EP2021/051845, filed on Jan. 27, 2021, and claims priority to Application no. DE 10 2020 102 471.1, filed in the Federal Republic of Germany on Jan. 31, 2020, the disclosures of which are expressly incorporated herein in their entirety by reference thereto.

TECHNICAL FIELD

The present disclosure relates to a method according to the present disclosure. It also relates to a control device or closed-loop control device according to the present disclosure and a medical set according to the present disclosure. Furthermore the present disclosure relates to a digital storage medium according to present disclosure, a computer program product according to the present disclosure, as well as a computer program according to the present disclosure.

BACKGROUND

Extracorporeal blood treatment using dialysis is known from practice. Whereby the patient's blood is withdrawn and extracorporeally fed along an blood circuit and through, e.g., a blood filter. The blood filter includes a blood chamber through which blood is guided, and a dialysis liquid chamber, through which dialysis liquid is guided. Both chambers are separated from each other by a semi-permeable membrane. Blood and dialysis liquid are mostly guided through the blood filter by the counter-current principle. The blood is purified in the blood filter, on exiting the blood filter the dialysis liquid, from now on referred to as effluate or effluent, is regarded as used and is discarded. In addition to the dialysate, the effluent to be discarded also includes filtrate (or ultra-filtrate), which includes water that has been withdrawn from the blood in the blood filter. Filtrate and dialysate will be referred to individually or collectively in the following simply as effluent. In addition to acute cases, dialysis is mainly used with patients who have end-stage renal failure.

Patients with end-stage renal failure are only partially able or are not at all able to excrete the toxins and fluids (water) that accumulate in the body. Therefore, these patients depend on the extracorporeal dialysis procedure to regularly reduce the accumulation of these substances. For this purpose, most of the patients typically undergo a hemodialysis treatment three times a week. In addition to the removal of substances such as urea and potassium, an essential object of dialysis is to reduce patient over-hydration due to fluid intake, by removing fluid from the blood so that the patient ideally regains his or her dry weight after dialysis.

In the body, water is distributed in different physiological compartments, which can be divided into the intracellular space, the extracellular space and the interstitium (Guyton & Hall, Textbook of Medical Physiology, Publisher Elsevier Saunders, Philadelphia (USA), 11. Edition, 2006). The distribution among these compartments is mainly determined by the osmotic equilibrium, to which the sodium content in these compartments is the main contributor. During hemodialysis, both an exchange of substances with the blood as well as a removal of fluid from the blood take place in the dialyzer. After the blood has been returned to the body, a new equilibrium is established by the flow of fluid from other parts of the body and by balancing the substance concentration. However, these processes take a certain amount of time, so it may be that the removal of fluid from the blood by dialysis is faster than the flow of body water. Since this reduces the volume (or quantity) of water in the blood vessels, it leads to a drop in blood pressure, possibly critical drops in blood pressure, during dialysis.

SUMMARY

An object of the present disclosure is to recommend a method for determining a time point for the taking of a pressure measurement, e.g., a blood pressure measurement during the blood treatment session.

Furthermore, a control device or closed-loop control device, a medical set, a suitable digital storage medium, a suitable computer program product and a suitable computer program are to be specified.

The object according to the present disclosure may be achieved with the method, a control device or closed-loop control device and a medical set having the features of the present disclosure. Further, the object according to the present disclosure may be achieved with a digital storage medium, a computer program product, as well as a computer program according to the present disclosure.

The method according to the present disclosure relates to the determining of a time point to take a patient's pressure measurement, or recommending that a pressure measurement is taken. Hereby, the recommended time point and indirectly also the measuring time point, is or will be during a treatment session. The treatment of the patient is one in which the patient's blood is treated extracorporeally using a blood treatment apparatus, e.g., by performing the process of ultrafiltration.

The method according to the present disclosure encompasses monitoring (alternatively observing or following up) during the treatment session or at least during a phase of it, the ultrafiltration rate, with which the patient's blood is or will be treated, the patient's relative blood volume and/or a sodium concentration (in the following also: [Na$^+$]). The monitoring may be or encompass detecting a change in each of these values over a period of time.

In some embodiments, these values (ultrafiltration rate, relative blood volume and/or sodium concentration) or a change in them, are monitored for the existence of or for the fulfilling of a pre-determined criterion.

The method according to the present disclosure further encompasses transmitting a signal to a provided blood pressure measuring device. The signal is transmitted if, when or as soon as the pre-determined criterion for the ultrafiltration rate, for the relative blood volume, and/or for the sodium concentration or a change thereto is met.

Optionally, the method according to the present disclosure also encompasses providing the blood pressure measuring device, which is suitable and/or prepared for collecting the patient's blood pressure measurement readings.

The present disclosure further relates to a control device or closed-loop control device. It is configured or programmed to carry out and/or to initiate, e.g., on a blood pressure measuring device provided, the method according to embodiments of the present disclosure or their mechanical steps, e.g., in each of the embodiments described herein and in each possible combination of the herein disclosed features, e.g., method steps.

The control device or closed-loop control device may include devices or be connected in signal communication with such devices, which can execute the individual method steps or method features which are disclosed herein and are designed, configured and/or programmed accordingly for this purpose.

A medical set according to the present disclosure (herein also referred to as: set) includes a control device or closed-loop control device according to the present disclosure and a blood pressure measuring device. Thereby, the control device or closed loop-control device and the blood pressure measuring device are in signal communication with other.

In this context, a signal communication may encompass the sending and/or receiving or transmitting of information, as well as the exchange of information, or a configuration thereof. some embodiments, an example of information which the control device or closed-loop control device transmits to the blood pressure measuring device is a signal to prepare for a blood pressure measurement, e.g., a signal to inflate a blood pressure cuff. Alternatively or additionally, for example a blood pressure measurement collected by the blood pressure measuring device can be transmitted from the latter to the control device or closed-loop control device, for further processing, for example.

A digital, non-volatile storage medium, according to the present disclosure, in the form of a machine readable carrier, e.g., in the form of a diskette, storage card, CD, DVD Blu-ray disc or (E)EPROM, FRAM (Ferroelectric RAM) or SSD (Solid-State-Drive) with electronically readable control signals, may be configured to interact with a programmable control device or closed-loop control device in such a way that, so that the mechanical steps of the method according to the present disclosure are initiated.

Thereby, all, any or several of the steps, e.g., mechanical steps, of the method according to the present disclosure may be initiated.

Alternatively or additionally to this, the digital storage medium according to the present disclosure may be configured so that a conventional control device or closed-loop control device can be reprogrammed into a control device or closed-loop control device according to the present disclosure.

A computer program product according to the present disclosure includes a transient, volatile program code or a program code saved on a machine readable carrier for initiating the mechanical steps of the method according to the present disclosure, when the computer program product is running on a control device or closed-loop control device. Computer program product, for example, can be understood according to the present disclosure as a computer program stored on a carrier, an embedded system being a comprehensive system with a computer program (e.g., electronic device with a computer program), a network of computer-implemented computer programs (e.g., client/server-system, a cloud computing system etc.), or a computer on which a computer program is loaded, runs, stored, executed or developed.

Alternatively or additionally hereto, the computer program product according to the present disclosure may be configured to reprogram a conventional control device or closed-loop control device into a control device or closed-loop control device according to the present disclosure.

The term "machine-readable carrier" as it is used herein, refers in certain embodiments of the present disclosure to a carrier, which contains data or information interpretable by software and/or hardware. The carrier may be a data carrier, such as a diskette, a CD, DVD, a USB stick, a flashcard, an SD card or the like, as well as any other storage referred to herein or any other storage medium referred to herein.

A computer program according to the present disclosure includes a program code to initiate the steps of the method according to the present disclosure, e.g., the mechanical steps, when the computer program is running on a control device or closed-loop control device. According to the present disclosure, a computer program can be understood to mean, for example, a physical, ready-for-distribution software product that includes a program.

Alternatively or additionally, the computer program according to the present disclosure, may be configured in order to reprogram a conventional control device or closed-loop control device into a control device or closed-loop control device according to the present disclosure.

It also applies to the computer program product according to the present disclosure and the computer program according to the present disclosure, that all, any, or several of the steps, e.g., mechanical steps, of the method according to the present disclosure may be initiated.

Embodiments according to the present disclosure may include several, one or more of the aforementioned or following features in any combination, unless the person skilled in the art recognizes their combination as technically impossible. Embodiments according to the present disclosure are further subject-matter of the dependent claims.

In all of the following statements, the use of the expression "may be" or "may have" and so on, is to be understood synonymously with "preferably is" or "preferably has," and so on respectively, and is intended to illustrate an embodiment according to the present disclosure.

Whenever numerical words are mentioned herein, the person skilled in the art shall recognize or understand them as indications of a numerical lower limit. Unless it leads the person skilled in the art to an evident contradiction, the person skilled in the art shall comprehend the specification for example of "one" as encompassing "at least one". This understanding is also equally encompassed by the present disclosure as the interpretation that a numeric word, for example, "one" may alternatively mean "exactly one", wherever this is evidently technically possible for the person skilled in the art. Both are encompassed by the present disclosure and apply herein to all numerical words used.

Whenever an embodiment is mentioned herein, it is then an exemplary embodiment according to the present disclosure.

In some embodiments, the criterion does not include, or encompass, determining a time point for measuring a patient's blood pressure.

In some embodiments, the criterion is not or does not encompass a time criterion, such as the question of whether a predetermined period of time has elapsed since a predetermined event, a time, or a previous pressure measurement.

In some embodiments, the blood pressure measuring device is part of the blood treatment apparatus, or is in signal communication with it during the treatment session, and/or it is configured for this and/or appropriately adapted to the blood treatment apparatus, assigned to or "paired" with it.

In some embodiments, the method does not encompass an automatic blood pressure measurement, which takes place, for example, according to predefined time criteria (e.g., such as every 5 minutes).

In some embodiments, the method does not include multiple blood pressure measurements, in which the interval between them is determined on the basis of a time measurement or only one time measurement.

In some embodiments, the blood treatment apparatus according to the present disclosure includes sensors inserted upstream and/or downstream of a dialyzer of the blood treatment apparatus to measure the electrolyte and/or fluid balance, e.g., on the dialysis liquid side or machine side and/or on the blood side. They can be used to determine the sodium concentration as discussed herein.

In some embodiments, in order to be controlled or regulated by it the blood treatment apparatus includes a control device or closed-loop control device. The control device or closed-loop control device may be a device according to the present disclosure. It may be programmed and/or configured in order to control or regulate the blood treatment device in addition to carrying out or causing the method according to the present disclosure in cooperation with other devices, such as a blood pressure measuring device.

The control device or closed-loop control device may be configured to transmit machine signals that are directed as control signals to the blood treatment apparatus based on input from the physician or, alternatively or additionally, it may be configured to generate said machine signals based on stored algorithms. In this way, the physician, for example, can specify which treatment profile should be used.

Input fields, switches, controls, etc. for the physician which are corresponding and optionally specifically provided for this purpose, may be included by the control device or closed-loop control device, a display device and/or a section of the blood treatment apparatus.

In some embodiments, the control device or closed-loop control device, the blood pressure measuring device, the set or the blood treatment apparatus include devices that are configured to carry out steps of the methods according to the present disclosure. This applies to every step disclosed herein.

In several embodiments, the method according to the present disclosure runs on a machine or computer. An input option for the user may be provided for required inputs. Output devices or display devices can be provided to display results of the method or treatment instructions.

In some embodiments of the method according to the present disclosure, the predetermined criterion for the ultrafiltration rate is met if the ultrafiltration rate, or a change in it, reaches or exceeds a minimum value.

The predetermined criterion for the ultrafiltration rate is fulfilled in some embodiments if the ultrafiltration rate or a change in it over or for a predetermined period of time is intended or aimed for.

Alternatively or additionally, in several embodiments the predetermined criterion for the relative blood volume is met when the relative blood volume or its measurement reading has reached or fallen below a minimum value, and/or when a change in it (i.e. its decrease or increase in value per time) has reached or exceeded a maximum value.

Again, in addition or alternatively, in some embodiments of the method, the predetermined criterion for the sodium concentration, e.g., the sodium concentration of the dialysis liquid or dialysate, is met if the sodium concentration falls below a minimum value or if the change in the sodium concentration exceeds a maximum value.

In addition or alternatively to this, the predetermined criterion for the ultrafiltration rate, for the relative blood volume, and/or for the sodium concentration, or the change in any of these, is met if a predetermined event for the ultrafiltration rate, for the relative blood volume and/or for the sodium concentration in the course of a treatment profile for the ultrafiltration rate occurs or is reached. The treatment profile is or will be set here on the blood treatment apparatus.

Each point in the treatment profile, represented as a curve over time, can be understood here as an event.

In several embodiments of the method according to the present disclosure, the signal to the provided blood pressure measuring device is or encompasses a signal that serves to prepare or initiate the preparation of the blood pressure measuring device for a blood pressure measurement. This preparation may be or include an inflation of an optional blood pressure cuff of the blood pressure measuring device.

In some embodiments, the signal to the provided blood pressure measuring device is, or encompasses, a signal to measure an arterial blood pressure measurement or to measure a venous blood pressure measurement of the patient or to prepare such a measurement. The signal may trigger such a measurement.

Based on the blood pressure readings taken on the one hand, and the overall circumstances that may have influenced the readings on the other, the physician can diagnose normotension, hypertension or, what is to be the more likely here, hypotension.

The circumstances that must be taken into account in order to make such a diagnosis include, amongst others, how the blood pressure readings of the patient can be classified in comparison with those of a collective, or whether they have changed over time. This process can be described as evaluation.

In several embodiments of the method according to the present disclosure, the monitoring of the ultrafiltration rate, the relative blood volume and/or the sodium concentration is or includes reading out at least one set treatment parameter or treatment profile or includes such a reading out, for example from the control device or closed-loop control device. This treatment profile can be preset and/or selected on the blood treatment apparatus used during the blood treatment session.

In some embodiments of the control device or closed-loop control device according to the present disclosure, it is optionally configured to process and/or evaluate the arterial blood pressure reading and/or the venous blood pressure reading.

Processing and/or evaluating the arterial blood pressure reading and/or the venous blood pressure reading can lead to the diagnosis of normotension, hypertension or hypotension.

In several embodiments of the control device or closed-loop control device according to the present disclosure, said device is optionally configured to trigger an alarm.

Alternatively or additionally, in some embodiments it is configured to cause an interruption or termination of the ultrafiltration.

In several embodiments, the control device or closed-loop control device, again in addition or alternatively, is provided and/or configured to initiate at least one new determining of a blood pressure measurement. The determining of the blood pressure measurement reading can be followed by the processing and/or evaluation thereof.

Alternatively or additionally, in some embodiments the control device or closed-loop control device is configured to administer a bolus or an on-line bolus.

For the administering of a bolus the following may apply: For the treatment, a sodium concentration of 130-145 mmol/l in the dialysis liquid is set as the starting value (depending on the experience with the respective patient using Kt/V measurement on the blood treatment apparatus or based on measured or determined blood values). The set Na-concentration can usually be adjusted to a maximum of 155 mmol/l, which occurs especially if a hypotonic state has been detected.

When administering the bolus, the bolus volume (usually substitution liquid, administered e.g., via an optional pre-dilution or post-dilution port or through a pre-dilution valve or a post-dilution valve) is between 30-240 ml. This is usually not balanced.

The administering of a bolus can be triggered on the basis of the values determined using conductivity sensors and optionally adjusted for volume and/or sodium content or salt content.

In several embodiments the control device or closed-loop control device according to the present disclosure is optionally provided and/or configured, to give an appropriate prompt for the attention of the user.

Alarm, interruption, termination, re-determining, bolus administration and/or notifications may be provided in case the evaluation of the arterial blood pressure reading and/or the venous blood pressure reading indicates that the patient is hypertonic or hypotonic or a predetermined range of permissible blood pressure measurements has been reached or exceeded, or the arterial blood pressure reading and/or the venous blood pressure reading is below a predetermined minimum value.

In some embodiments of the medical set according to the present disclosure, the set further includes a blood treatment apparatus. The blood treatment apparatus is used for extracorporeal treatment of a patient's blood by carrying out the process of ultrafiltration.

In several embodiments of the medical set the blood treatment apparatus is embodied as a hemodialysis apparatus, hemofiltration apparatus or as a hemodiafiltration apparatus, e.g., as an apparatus for the acute or for chronic renal replacement therapy. Thereby, the renal replacement therapy can include continuous or intermittent procedures.

In some embodiments the medical set according to the present disclosure includes sensors. These are optionally arranged and configured to measure the sodium concentration. The measurement is preferably carried out extracorporeally, e.g., in the dialysate.

The control device or closed-loop control device is in some embodiments additionally configured or programmed to control or regulate a blood treatment apparatus based on the results of the method. The controlling or regulating may be or encompass: interrupting or terminating the blood treatment or the ultrafiltration, reducing or regulating the ultrafiltration rate, re-determining the arterial blood pressure measurement and/or the venous blood pressure measurement, the administering of a saline bolus, treatment based on a modified treatment profile, changing the sodium concentration in the dialysis liquid, especially based on the physician's recommendation, and so on.

Whenever a suitability or a method step is mentioned herein, the present disclosure also includes corresponding programming or a configuration of a suitable device according to the present disclosure or a section thereof.

The determining of the relative blood volume is required regularly to control the fluid removal in the treated patients. As a result of ultrafiltration, the blood volume and thus the relative blood volume decrease. Changes in blood volume have an important impact on a patient's intradialytic blood pressure (Drukker, Parsons and Maher, Replacement of Renal Function by Dialysis, Kluwer Academic Publishers, Dordrecht, 5th Edition, 2004). The relative blood volume (short: RBV) can be determined, for example, based on the measurement of the hematocrit:

8

$$RBV = \left(\frac{HTC_0}{HTC_1} - 1\right) \cdot 100$$

wherein the following applies:
HTC$_0$ is the haematocrit value at the time point t=0 (at the start of the treatment) and
HTC$_1$ is the hematocrit value at the current time point To determine the relative blood volume different physical methods may be used, for example, measuring the electrical conductivity, optical density, blood viscosity or physical density, e.g., by measuring the sound velocity and/or sound propagation. According to the present disclosure devices for example sensors, are provided for determining and/or monitoring the relative blood volume. Reference is made here to the prior art. Such devices are herein also referred to as blood volume monitors. According to the present disclosure, such a blood volume monitor may be provided.

Some or all of the embodiments of the present disclosure may have one, several or all of the advantages listed above and/or below.

An advantage of embodiments of the present disclosure may be improved patient monitoring during a blood treatment session, as the patient monitoring takes place during the critical moments of such a blood treatment session.

With embodiments of the present disclosure it can be advantageously avoided that, due to a lowering of the ultrafiltration rate during the treatment session which was erroneously considered necessary, or the administering of a saline bolus not related to blood pressure, a patient is released from the blood treatment session with excess fluid. Patient tolerance to the blood treatment session can thus be indirectly increased, which can noticeably improve the patient's quality of life.

By using embodiments of the present disclosure, e.g., by automating the determining of the appropriate, variable time points and with the advantages associated with early detection of pressure changes during a patient's blood treatment session, even without the intervention of the personnel, unnecessary stress for the personnel can advantageously be avoided.

As a further advantage, the saving of time and attention on the part of the personnel is possible at this point.

Through embodiments of the present disclosure, higher ultrafiltration volumes or rates can advantageously be sought without risking any discomfort to the patient. Moments in which he might feel uncomfortable due to a too high ultrafiltration volume or an too high ultrafiltration rate can be detected at an early stage according to the present disclosure and thus ultimately advantageously avoided.

A further advantage of embodiments of the present disclosure is that they are easy to implement.

In practice, the current relative blood volume or its rate of change is regularly compared with a threshold value that is individually defined for the patient, and the rate of fluid withdrawal is reduced when the threshold value is exceeded. This can lead to the fact that at the end of the dialysis the volume of fluid withdrawn is lower than planned and the dry weight is therefore not reached. According to the present disclosure, these circumstances can advantageously be avoided as, for example, the ultrafiltration rate required to achieve the dry weight in the time available can be applied. If any discomfort should arise, this could be recognized according to the present disclosure. In this way, the ultrafiltration rate does not have to be reduced purely prophylactically to avoid any discomfort on the part of the patient.

All advantages achievable with the method according to the present disclosure can also be achieved undiminished with the devices according to the present disclosure, and vice versa.

BRIEF DESCRIPTION OF THE FIGURES

The present disclosure is exemplarily explained with regard to the accompanying drawings in which same reference numerals refer to the same or similar components. In the figures the following applies.

DETAILED DESCRIPTION

Figure 1:
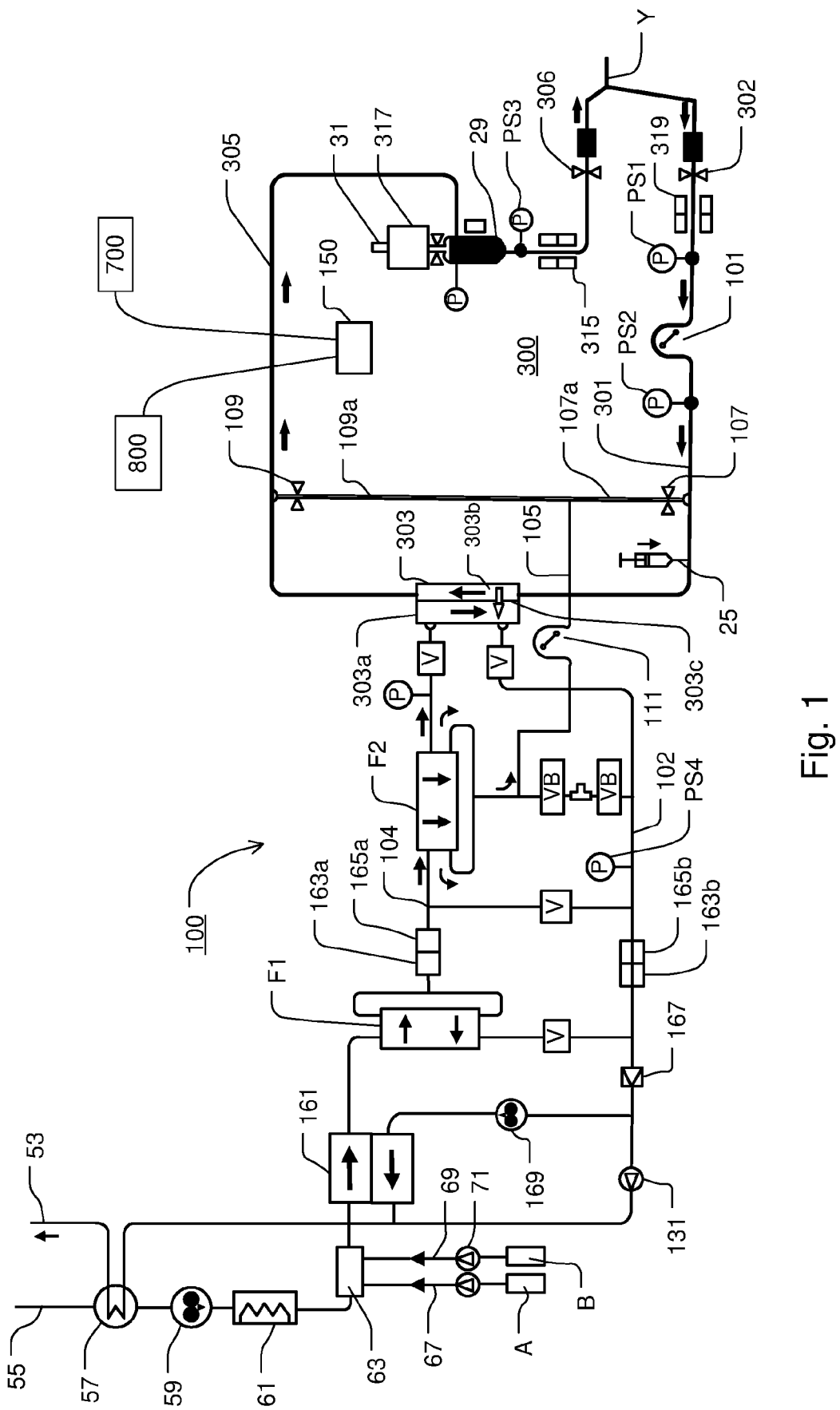
FIG. 1 shows in a simplified, schematic representation a blood treatment apparatus according to the present disclosure with an extracorporeal blood circuit in a first embodiment or the representation of a flow diagram of a blood treatment apparatus according to the present disclosure, exemplarily embodied as a hemodiafiltration apparatus.

FIG. 1 shows an extracorporeal blood circuit 300, which can be connected to the vascular system of the patient (not shown) for a treatment via double-needle access, or via single-needle access, using, for example, an additional Y-connector (reference numeral Y) as shown in FIG. 1. The blood circuit 300 can optionally be present in sections thereof in or on a blood cassette.

Pumps, actuators and/or valves in the area of the blood circuit 300 are connected to a blood treatment apparatus 100 according to the present disclosure or for example, to a control device 150 included within.

The blood circuit 300 includes (or is connected to) an arterial patient tubing clamp 302 and an arterial connection needle of an arterial section or of an arterial patient line, a blood withdrawal line or a first line 301. The blood circuit 300 further includes (or is connected to) a venous patient tubing clamp 306 and a venous connection needle of a venous section, a venous patient line, blood return line or second line 305.

A blood pump 101 is provided in or on the first line 301, a substitute pump 111 is connected to a dialysis liquid inlet line 104 for conveying fresh dialysis liquid, which is filtered through a further filter (F2) (substituate). A substitute line 105 can be in fluid communication with the inlet line 104. Using the substitute pump 101, substitute can be introduced by pre-dilution via a pre-dilution valve 107, or by post-dilution via a post-dilution valve 109, into line sections via corresponding lines 107a or 109a, for example into the arterial line section 301 or into the venous line section 305 (here between a blood chamber 303b of a blood filter 303 and a venous air separation chamber or venous blood chamber 29) of the blood circuit 300

The blood filter 303 includes the blood chamber 303b which is connected to the arterial line section 301 and the venous line section 305. A dialysis liquid chamber 303a of the blood filter 303 is connected to the dialysis liquid inlet line 104 leading to the dialysis liquid chamber 303a and a dialysate outlet line 102 leading away from the dialysis liquid chamber 303a which guides dialysate, i. e. used dialysis liquid. Dialysis liquid chamber 303a and blood chamber 303b are separated by a mostly semi-permeable membrane 303c. This membrane is what separates the blood side with the extracorporeal blood circuit 300 and the machine side with the dialysis liquid circuit or dialysate circuit, which is shown in FIG. 1 to the left of the membrane 303c.

The arrangement in FIG. 1 encompasses an optional detector 315 for detecting air and/or blood. The arrangement in FIG. 1 further encompasses one or two pressure sensors PS1 (upstream of the blood pump 101) and PS2 (downstream of the blood pump 101, which measures the pressure upstream of the blood filter 303 ("pre-hemofilter")) at the positions shown in FIG. 1. Further pressure sensors may be provided, e.g., the pressure sensor PS3 downstream of the venous blood chamber 29.

An optional single-needle-chamber 317 is used in FIG. 1 as a buffer and/or a compensating reservoir in a single-needle procedure in which the patient is connected to the extracorporeal blood circuit 300 via only one of the two blood lines 301, 305.

The arrangement in FIG. 1 additionally includes an optional detector 319 for detecting air bubbles and/or blood.

An addition point 25 for Heparin may be optionally provided.

Shown on the left in FIG. 1 is a mixing device 63 which, from containers A (for A concentrate via the concentrate supply 67) and B (for B concentrate via the concentrate supply 69), provides a predetermined mixture for the respective solution for use by the blood treatment device 100 provides. The solution contains, in the heater 61 for example, warmed water from the water source 55 (on-line, e.g., as reverse osmosis water or from bags).

A pump 71, that may be referred to as a concentrate pump or sodium pump is in fluid communication with the mixing apparatus 63 and with a source having sodium, such as the container B, and/or conveys therefrom.

Furthermore, an outlet 53 for the effluent can be seen in FIG. 1. An optional heat exchanger 57 and a first flow pump 59, which is suitable for de-gassing, complete the arrangement shown.

A further pressure sensor for measuring the filtrate pressure or the membrane pressure of the blood filter 303 may be provided as PS4 downstream of the blood filter 303 on the water-side, however preferably upstream of the ultrafiltration pump 131 in the dialysate outlet line 102. Further optional pressure measuring points P may also be provided.

Blood, which leaves the blood filter 303, passes through an optional venous blood chamber 29, which can include a de-aeration device 31 and/or may be in fluid communication with a further pressure sensor PS3.

The exemplary arrangement shown in FIG. 1 includes a control device or closed-loop control device 150. This can be in wired or wireless signal communication with any of the components referred to herein—such as to the blood pump 101—in order to control or regulate the blood treatment apparatus 100. It is optionally configured in order to carry out the method described herein, e.g., automatically.

By using the device for on-line mixing of the dialysis liquid, a variation in the sodium content thereof controlled by the control device 150, is possible within certain limits. For this purpose, measurements determined via the conductivity sensors 163a, 163b may be taken into account. Should an adjustment of the sodium content of the dialysis liquid (sodium concentration) or of the substitute be required or desired, this can be done by adjusting the delivery rate of the sodium pump 71.

Furthermore, the blood treatment apparatus 100 includes means for conveying fresh dialysis liquid as well as dialysate. For this purpose, the first flow pump 59, which conveys fresh dialysis liquid towards the blood filter 303, is provided upstream of the blood filter 303. A first valve may be provided between the first flow pump 59 and the blood filter 303, which opens or closes the inlet to the blood filter 303 on the inlet side. A second optional flow pump 169 is provided, for example downstream of the blood filter 303, which conveys dialysate to the outlet 53. A second valve may be provided between the blood filter 303 and the second flow pump 169, which opens or closes the outlet on the outlet side.

Furthermore, the blood treatment apparatus 100 optionally includes a device 161 for balancing the flow going into and coming out of the dialyzer 303 on the machine side. The device 161 for balancing is preferably arranged in a line section between the first flow pump 59 and the second flow pump 169.

The blood treatment apparatus 100 further encompasses means, such as the ultrafiltration pump 131, for the precise removal of a fluid volume from the balanced circuit as specified by the user and/or by the control device 150.

Sensors such as the optional conductivity sensors 163a, 163b serve to determine the conductivity, which in some embodiments is temperature-compensated, as well as the liquid flow upstream and downstream of the dialyzer 303.

Temperature sensors 165a, 165b can be provided individually or in groups. Temperature readings supplied by them can be used according to the present disclosure to determine a temperature-compensated conductivity.

A leakage sensor 167 is optionally provided.

Further flow pumps, in addition or as an alternative to, the one indicated with the reference numeral 169 for example, can also be provided.

A row of optional valves is each indicated in FIG. 1 with a V. By pass valves are indicated with a VB.

In some embodiments the control device 150 determines the electrolyte and/or liquid balancing based on the measurement readings of the afore-mentioned, optional sensors.

Filters F1 and F2 may be provided in series-connection.

The filter F1 here serves exemplarily, via the mixing apparatus 63, to produce sufficiently pure dialysis liquid, even when using impure water, which then flows through the blood filter 303, e.g., according to the counter-current principle.

Exemplarily, here the filter F2 serves to generate a sterile or sufficiently filtered substitute from the sufficiently pure dialysis liquid, which leaves the first filter F1, by filtering out pyrogenic substances, for example. This substitute can safely be added to the patient's blood flowing extracorporeally and thus ultimately be supplied to the patient's body.

FIG. 1 shows that the control device 150 of the blood treatment apparatus 100 may be in wired or wireless signal communication with a blood pressure measuring device 700 and/or with a blood volume monitor 800 and is configured and prepared for this, for example, through corresponding mutual programming and coordination.

The optional blood treatment apparatus 100 of the set according to the present disclosure is shown in FIG. 1 as a device for hemo(dia)filtration. However, hemodialysis devices also fall within the scope of the present disclosure, even though they are not specifically shown in the figures.

The present disclosure is not limited to the embodiment described above, this serves only as an illustration.

The arrows shown in FIG. 1 generally indicate the direction of flow in FIG. 1.

Figure 2:
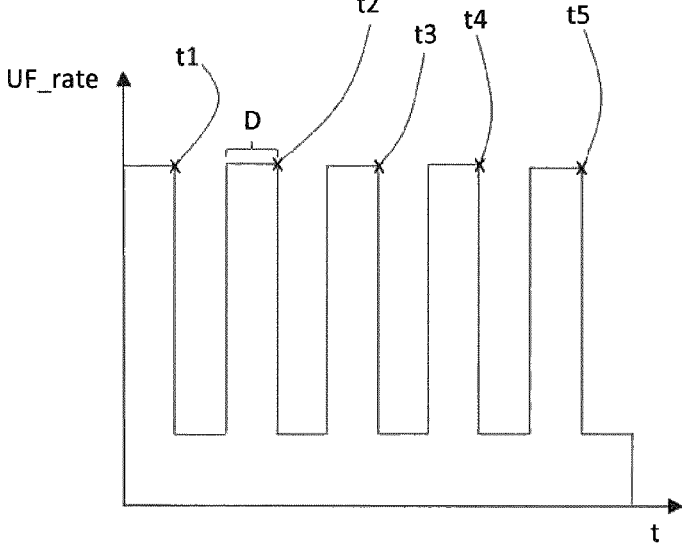
FIG. 2 shows examples of the implementation of the method according to the present disclosure with reference to a graphical representation of an exemplary treatment profile.

FIG. 2 shows examples for time points t1, . . . , t5, set according to the present disclosure, within the time sequence of an exemplary treatment profile, wherein the pre-determined ultrafiltration rate UF_rate of this treatment profile (e.g., in the unit ml/h) is shown over time t (e.g., in the unit h).

Such a treatment profile may be stored on the blood treatment apparatus and can be selected by the physician or qualified treatment personnel for the treatment of a specific patient.

The example given shows a treatment profile with alternating, clear changes between lower and higher ultrafiltration rates UF_rate. The sections of the treatment profile with the higher ultrafiltration rates can also be referred to as peaks, since they correspond to peaks of the ultrafiltration rate UF_rate over the course of the treatment profile over time.

The method according to the present disclosure can, with knowledge of and due to the stored treatment profile or its pre-determined course, determine ad hoc or in advance at which time points t1, . . . T5 measuring a patient's blood pressure measurement is considered useful according to the present disclosure. Since especially high ultrafiltration rates UF_rate are usually less tolerated by the (respective) patient, the end of such a peak is likely to determine the current condition of the patient, e.g., to allow his current blood pressure readings to be determined. These time points t1, . . . , t5 are marked with an "x" in the diagram in FIG. 2.

Alternatively or additionally, if the course of the treatment profile is known, the duration D of such a peak can be used to determine at least one time point t1, . . . , t5. For the sake of clarity, the duration D is only indicated with a reference numeral at one peak in FIG. 2.

A corresponding signal sent to the blood pressure measuring device 700 at such a time point t1, . . . t5 can lead—after the method—to the measurement of a blood pressure reading. After processing the measured blood pressure reading, for example in the control device or closed-loop control device 150 (see FIG. 1), this can lead to selecting an alternative treatment profile (see FIGS. 3a and 3b) or to changing the course of the selected treatment profile (see FIG. 4), with which treatment should preferably be continued in the further course of the blood treatment session.

The number of the set time points according to the present disclosure (here 5) is purely as an example and is not in any way to be understood as limiting.

Figure 3A:
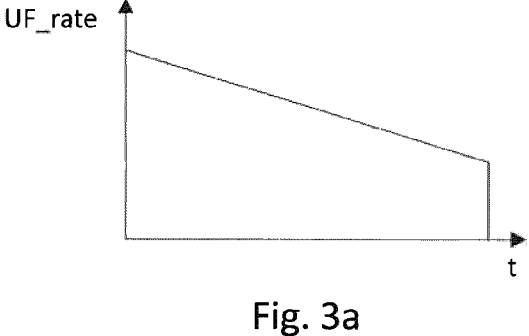
FIG. 3a shows a first alternative treatment profile of a blood treatment using ultrafiltration.

FIG. 3a shows a first alternative treatment profile of a blood treatment using ultrafiltration.

A blood pressure reading, measured at a time point set using the method according to the present disclosure, may show that the ultrafiltration rate UF_rate of the selected treatment profile (e.g., the treatment profile with alternating changes shown in FIG. 2) is not sufficiently well tolerated by the patient being treated. A linear course of the ultrafiltration rate UF_rate should be exemplarily shown here, which could be used as a first alternative treatment profile if the above-mentioned criteria are met. As can easily be seen, the ultrafiltration rate UF_rate in this example of a treatment profile decreases linearly from the beginning to the end during the blood treatment session.

It can be assumed that a decreasing ultrafiltration rate UF_rate can be more easily tolerated by a patient who did not perform as well with the treatment profile of FIG. 2.

Figure 3B:
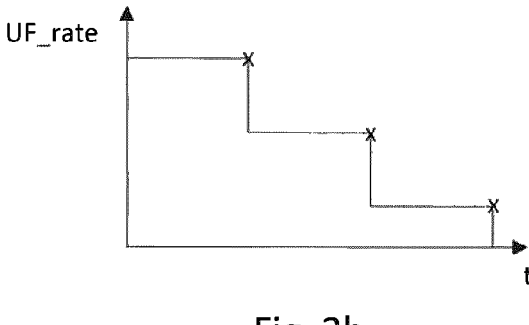
FIG. 3b shows a second alternative treatment profile of a blood treatment using ultrafiltration.

FIG. 3b shows a second alternative treatment profile of a blood treatment using ultrafiltration.

Similarly to FIG. 3a, it is again assumed in this example that the ultrafiltration rate UF_rate of the selected treatment profile (for example the treatment profile with alternating changes of FIG. 2) was not sufficiently well tolerated by the patient being treated. A step-shaped course of the ultrafiltration rate UF_rate should be mentioned here as an example of a second alternative treatment profile, which could be used if the above-mentioned criteria are met. As can easily be seen, in this example of a treatment profile during the blood treatment session the ultrafiltration rate UF_rate exemplarily decreases two times, each time by one level from the beginning to the end.

Here, too, it can be assumed that the decreasing ultrafiltration rate UF_rate can be more easily tolerated by the patient being treated. According to the present disclosure, at the time points marked "x" which can be determined by the method according to the present disclosure, a signal is again sent to the blood pressure measuring device 700, which can be followed by a determination of a further blood pressure reading and its evaluation and/or processing. According to the present disclosure, provision may be made so that the ultrafiltration rate UF_rate is reduced or maintained at these stages in accordance with the determined blood pressure readings.

In some embodiments, increasing the ultrafiltration rate UF_rate again or returning to a previously used treatment profile may be considered, based on the determining and evaluation or processing of blood pressure measurement readings.

Figure 4:
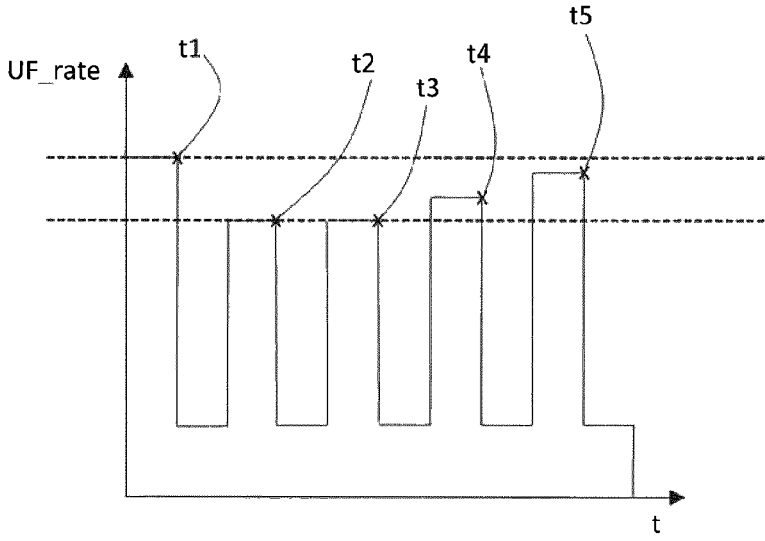
FIG. 4 shows an example for determining time points (t1, . . . , t5) within a blood treatment using ultrafiltration in a graphical representation of a exemplary treatment profile, which has been adapted based on the method according to the present disclosure.

FIG. 4 shows an example for determining time points t1, . . . , t5 during a blood treatment session using ultrafiltration in a graphical representation of an exemplary treatment profile, adapted according to the present disclosure.

As in FIG. 3a, in this example it is again assumed that the ultrafiltration rate UF_rate of the selected treatment profile (e.g., the treatment profile in FIG. 2 with alternating changes) was not sufficiently well tolerated by the patient being treated, this was detected at the first time point t1. In contrast to the treatment profile in FIG. 2, the treatment profile selected by the physician is amended accordingly so that the height of the peaks of the ultrafiltration rate UF_rate are adjusted, for example lowered, on the basis of the blood pressure reading which was determined at time point t1, that was determined according to the present disclosure. The different heights of the peaks of the ultrafiltration rate UF_rate before and after the adjustment of the ultrafiltration rate UF_rate are illustrated in FIG. 4 by two horizontal dotted lines.

In such embodiments, it is possible to again adjust the ultrafiltration rate UF_rate upwards if it is well tolerated by the patient, i.e. in connection with later measured, once again acceptable blood pressure readings. This is indicated in FIG. 4 in the course of the treatment profile over time following the time points t3 and t4 which are marked with "x".

Figure 5:
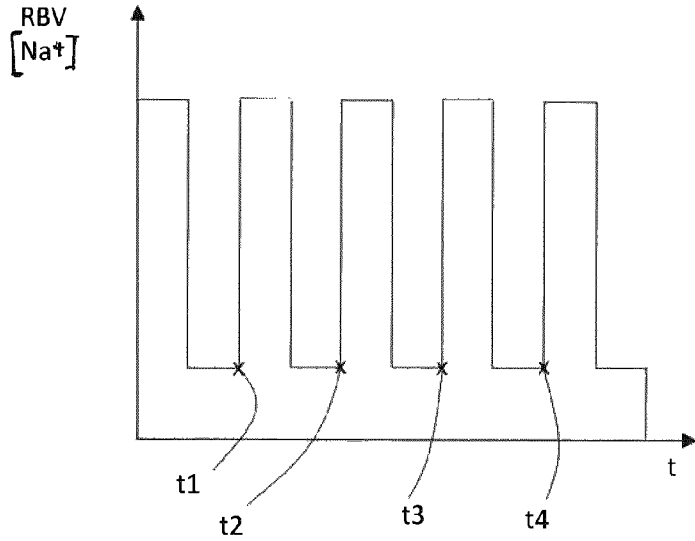
FIG. 5 shows examples of the implementation of the method according to the present disclosure with reference to a graphic representation of a further exemplary treatment profile.

FIG. 5 shows that the statements made here in the description of the figures regarding the criteria of the ultrafiltration rate UF_rate also apply without restriction to the criteria of the relative blood volume RBV or the criteria of the sodium concentration [Na+] within a blood treatment session.

LIST OF REFERENCE NUMERALS 25 addition point for Heparin (optional)
29 venous blood chamber (optional)
31 de-aeration device
53 outlet
55 water source
57 heat exchanger
59 first flow pump
61 heat apparatus
63 mixing apparatus
67 concentrate supply
69 concentrate supply
71 concentrate pump; sodium pump
100 blood treatment apparatus
101 blood pump
102 dialysate outlet line, effluent inlet line
104 dialysis liquid inlet line
105 substituate line
107 pre-dilution valve
107a line
109 post-dilution valve
109a line
111 pump for substituate
121 pump for dialysis liquid
131 pump for dialysate or effluent
150 control device or closed-loop control device
161 device
163a conductivity sensor
163b conductivity sensor
165a temperature sensor
165b temperature sensor
167 leakage sensor
169 second flow pump
300 extracorporeal blood circuit
301 first line (arterial line section)
302 first tubing clamp
303 blood filter or dialyzer
303a dialysis liquid chamber
303b blood chamber
303c semi-permeable membrane
305 second line (venous line section)
306 (second) tubing clamp
315 detector
317 single-needle-chamber
319 detector
700 blood pressure measuring device
800 blood volume monitor
F1 filter
F2 filter
A container
B container
D pre-determined duration
[Na+] sodium concentration
P pressure measuring points
PS1 arterial pressure sensor (optional)
PS2 arterial pressure sensor (optional)
PS3 pressure sensor (optional)
PS4 pressure sensor for measuring the filtrate pressure (optional)
RBV relative blood volume
t1 time point
UF_rate ultrafiltration rate V valves
VB bypass valves
Y Y-connector

The invention claimed is:

1. A method for determining or recommending at least one time point for measuring pressure measurements on a patient during a treatment session in which the patient's blood is treated extracorporeally via a blood treatment apparatus, the method comprising:

monitoring, during the treatment session, one or more of an ultrafiltration rate with which the patient's blood is treated and a sodium concentration for one or more changes in one or more of the ultrafiltration rate and the sodium concentration, respectively, or for fulfilling one or more pre-determined criteria, respectively, for one or more of the ultrafiltration rate and the sodium concentration; and transmitting a signal to a blood pressure measuring device when any of the one or more pre-determined criteria or any of the one or more changes are met, respectively, for one or more of the ultrafiltration rate and the sodium concentration, wherein the signal comprises an instruction for measuring a blood pressure of the patient at an end point of a peak of a plurality of peaks of a treatment profile of the ultrafiltration rate or of the sodium concentration or at an end point of a valley of a plurality of valleys of the treatment profile.

2. The method according to claim 1, wherein the patient's blood is treated extracorporeally via the blood treatment apparatus by carrying out an ultrafiltration process.

3. The method according to claim 1, wherein a pre-determined criterion for the ultrafiltration rate is met when a minimum value for the ultrafiltration rate or a change in the ultrafiltration rate is reached, exceeded, or set for a pre-determined duration.

4. The method according to claim 1, wherein a pre-determined criterion for the sodium concentration is met when the sodium concentration falls below a minimum value or when a maximum value for a change in the sodium concentration has been exceeded.

5. The method according to claim 4, wherein the pre-determined criterion for the sodium concentration is met when the sodium concentration falls below the minimum value in dialysis liquid or when the maximum value for the change in the sodium concentration in the dialysis liquid has been exceeded.

6. The method according to claim 1, wherein a change in or a pre-determined criteria for the ultrafiltration rate or the sodium concentration is met if a pre-determined event occurs or is reached during a blood treatment profile that is set on the blood treatment apparatus for the ultrafiltration rate or the sodium concentration, respectively.

7. The method according to claim 1, wherein the signal transmitted to the blood pressure measuring device comprises a signal for preparing the blood pressure measuring device for a procedure for measuring blood pressure readings of the patient.

8. The method according to claim 7, wherein the procedure comprises inflating a blood pressure cuff of the blood pressure measuring device.

9. The method according to claim 1, wherein the signal transmitted to the blood pressure measuring device comprises a signal for measuring a patient's arterial blood pressure reading or venous blood pressure reading.

10. The method according to claim 1, wherein monitoring one or more of the ultrafiltration rate and the sodium concentration comprises reading out at least one treatment parameter or treatment profile that is set on the blood treatment apparatus and used during the blood treatment session.

11. The method of claim 1, wherein the method excludes automatically measuring a blood pressure of the patient according to a predefined periodic time criteria.

12. The method of claim 1, wherein the plurality of peaks comprises peaks having a substantially equal, constant value.

13. The method of claim 1, wherein a first peak of the plurality of peaks has a first peak value, and wherein a second peak of the plurality of peaks has a second peak value that is different from the first peak value.

14. The method of claim 1, wherein the method further comprises:

processing a blood pressure measurement after transmitting the signal to the blood pressure measuring device; and based on the blood pressure measurement, selecting an alternative treatment profile of the ultrafiltration rate or of the sodium concentration or changing the treatment profile of the ultrafiltration rate or of the sodium concentration.

15. A control device or closed-loop control device configured to carry out mechanical steps of a method for determining or recommending at least one time point for measuring pressure measurements on a patient during a treatment session in which the patient's blood is treated extracorporeally via a blood treatment apparatus, the method comprising:

monitoring, during the treatment session, one or more of an ultrafiltration rate with which the patient's blood is treated and a sodium concentration for one or more changes in one or more of the ultrafiltration rate and the sodium concentration, respectively, or for fulfilling one or more pre-determined criteria, respectively, for one or more of the ultrafiltration rate and the sodium concentration; and transmitting a signal to a blood pressure measuring device when any of the one or more pre-determined criteria or any of the one or more changes are met, respectively, for one or more of the ultrafiltration rate and the sodium concentration, wherein the signal comprises an instruction for measuring a blood pressure of the patient at an end point of a peak of a plurality of peaks of a treatment profile of the ultrafiltration rate or of the sodium concentration or at an end point of a valley of a plurality of valleys of the treatment profile.

16. The control device or closed-loop control device according to claim 15, wherein the patient's blood is treated extracorporeally via the blood treatment apparatus by carrying out an ultrafiltration process.

17. The control device or closed-loop control device according to claim 15, wherein the control device or closed-loop control device is configured for one or both of processing and evaluating one or both of an arterial blood pressure reading and a venous blood pressure reading.

18. The control device or closed-loop control device according to claim 17, wherein the control device or closed-loop control device is configured to trigger an alarm, to cause an interruption or a termination of an ultrafiltration, to cause another blood pressure measurement to be determined and to evaluate the other blood pressure measurement, to cause an on-line bolus to be administered, and/or to output corresponding information for attention of a user should an evaluation of the arterial blood pressure reading and/or of the venous blood pressure reading show that the patient's blood pressure has reached or is no longer within pre-determined ranges.

19. A medical set comprising:

a blood pressure measuring device; and a control device or closed-loop control device configured to carry out mechanical steps of a method for determining or recommending at least one time point for measuring pressure measurements on a patient during a treatment session in which the patient's blood is treated extracorporeally via a blood treatment apparatus, the method comprising:

monitoring, during the treatment session, one or more of an ultrafiltration rate with which the patient's blood is treated and a sodium concentration for one or more changes in one or more of the ultrafiltration rate and the sodium concentration, respectively, or for fulfilling one or more pre-determined criteria, respectively, for one or more of the ultrafiltration rate and the sodium concentration; and transmitting a signal to a blood pressure measuring device when any of the one or more pre-determined criteria or any of the one or more changes are met, respectively, for one or more of the ultrafiltration rate and the sodium concentration, wherein the signal comprises an instruction for measuring a blood pressure of the patient at an end point of a peak of a plurality of peaks of a treatment profile of the ultrafiltration rate or of the sodium concentration or at an end point of a valley of a plurality of valleys of the treatment profile.

20. The medical set according to claim 19, wherein the patient's blood is treated extracorporeally via the blood treatment apparatus by carrying out an ultrafiltration process.

21. The medical set according to claim 19, further comprising the blood treatment apparatus.

22. The medical set according to claim 21, wherein the blood treatment apparatus comprises a hemodialysis apparatus, a hemofiltration apparatus, or a hemodiafiltration apparatus for acute or chronic renal replacement therapy.

23. The medical set according to claim 22, wherein the renal replacement therapy comprises continuous or intermittent procedures.

24. The medical set according to claim 19, further comprising sensors arranged and configured to extracorporeally measure the sodium concentration in dialysis liquid or in dialysate and/or measure a relative blood volume.

* * * * *